United States Patent [19]

Williams, Jr.

[11] 4,376,666
[45] Mar. 15, 1983

[54] PROCESS FOR THE RECOVERY OF CARBORANE FROM REJECT PROPELLANT

[75] Inventor: Leroy J. Williams, Jr., Huntsville, Ala.

[73] Assignee: The United States of America as represented by the Secretary of the Army, Washington, D.C.

[21] Appl. No.: 194,192

[22] Filed: Oct. 6, 1980

[51] Int. Cl.³ .......................................... D03D 23/00
[52] U.S. Cl. .................................. 149/109.6; 86/1 B; 149/22; 149/76; 264/3 C
[58] Field of Search ........................ 149/109.6, 76, 22; 86/1 B; 264/3 C

[56] References Cited

U.S. PATENT DOCUMENTS

| | | | |
|---|---|---|---|
| 3,702,271 | 11/1972 | Henderson et al. | 149/109.6 |
| 3,897,237 | 7/1975 | Musselman et al. | 149/109.6 |
| 3,930,844 | 1/1976 | Parrish | 149/109.6 |
| 3,982,930 | 9/1976 | Doades et al. | 149/109.6 |

Primary Examiner—Stephen J. Lechert, Jr.
Attorney, Agent, or Firm—Nathan Edelberg; Robert P. Gibson; Jack W. Voigt

[57] ABSTRACT

Disclosed is a process for the recovery of carborane from reject solid propellant. The process comprises slicing or shredding into small pieces the solid propellant under water, screening the propellant to remove water from the propellant, performing a pentane extraction of the carborane from the small pieces of propellant, diluting the carborane/pentane solution with additional pentane and the carborane/pentane solution to remove small particles of propellant and other solids such as ammonium perchlorate, allowing the filtering effluent of carborane/pentane solution to enter a water wash tank at the bottom to remove ammonium perchlorate and other water soluble propellant materials, allowing the carborane/pentane layer to separate from the water layer, and then siphoning the carborane/pentane solution from the water layer, and distilling the pentane to separate and recover the carborane.

4 Claims, 3 Drawing Figures

RECOVERY OF NHC FROM PROPELLANT

RECOVERY OF NHC FROM PROPELLANT

PROCESS FOR THE RECOVERY OF CARBORANE FROM REJECT PROPELLANT

DEDICATORY CLAUSE

The invention described herein may be manufactured, used, and licensed by or for the Government for governmental purposes without the payment to me of any royalties thereon.

BACKGROUND OF THE INVENTION

Solid propellant compositions have been developed which possess a wide range of chemical and mechanical properties that meet a wide range of performance parameters. Additive compounds for propellants have played a vital role in achieving these chemical and mechanical properties.

In recent years carborane chemistry as applied to solid propellant technology has been of particular interest. N-hexylcarborane which is prepared by the reaction of a decaborane ligand with n-octyne is a preferred carborane additive compound for propellant use. The decaborane ligands which have been most widely used are acetonitrile and diethylsulfide; other decaborane ligands can be prepared or selected from those reported in the literature.

N-hexylcarborane (NHC) is used in solid rocket propellants as a ballistic modifier and as a plasticizer to improve propellant mechanical properties. The cost to achieve these mechanical properties are quite high because of the limited production since at present there are no major commercial applications for the boron derivatives and carboranes. Present estimates indicate that the production cost of NHC will be as much as $400.00 per pound compared to the conventional propellant ingredients which cost in the order of $1.00 to $5.00 per pound. Although the NHC is used in relative small quantities, it has a very significant influence on the cost of the propellant because of its unusually high cost.

In the manufacture of solid rocket propellants, there is always some waste/scrap propellant along with some rejected motors. Because of the high cost of the NHC, methods to recover the NHC need to be developed and demonstrated to provide data to show that it is economically feasible and worth while to recover NHC for reuse. Recovery of NHC could be obtained from waste propellant, propellant test specimen, reject motors and rejected propellant, both cured and uncured material.

The recovery of carborane from reject propellant and motors could offer an advantage in the reduction of the manufacturing cost of missiles. For the recovery process to be an effective cost saving operation, the carborane must be recovered and purified for reuse. The cost of the operation must be such that the recovered carborane is much cheaper than the carborane obtained from production.

An object of this invention is to provide a process for the recovery of carborane from reject propellant from various sources including waste propellant, propellant test specimen, and reject motors, both cured and uncured materials.

A further object of this invention is to provide a process particularly adapted for the recovery of a preferred carborane, n-hexylcarborane, from reject propellant.

Another object of this invention is to provide a process which includes provisions for recycling the extraction solvent compounds employed to recover the carborane compound to thereby improve the cost effectiveness of the overall process.

SUMMARY OF THE INVENTION

The process of this invention comprises slicing or shredding into small pieces e.g., a solid propellant composition containing the carborane compound to be recovered. The slicing or shredding is accomplished under water for safety purposes plus the additional advantage of removing some water soluble propellant ingredients. The water and sliced propellant suspension is then screened to remove the water from the propellant. The screened propellant (which contains the desirable carborane compound) is extracted with pentane or hexane solution for a predetermined time of up to about 27 hours and a major portion of the propellant solids is removed as waste. The pentane/carborane solution is then diluted with additional pentane and the solution with finely suspended solids is then transferred to a wash tank (bottom) through a dip tube. The wash tank contains water which will remove the finely suspended ammonium perchlorate and other water soluble materials. This water-pentane-carborane mixture should not be stirred; otherwise, a very hard to break emulsion will form. The pentane/carborane layer is allowed to separate from the water layer, and then the pentane/carborane layer is siphoned from the water layer, and the water is sent to waste disposal. The carborane/pentane solution is transferred to the carborane recovery still for concentration by flash distilling of about 80% of the pentane to yield about 80/20 solution of carborane/pentane. The 80/20 solution is transferred to another still for further distillation and purification.

DESCRIPTION OF THE PREFERRED EMBODIMENT

The process for the recovery of carborane (n-hexylcarborane) from reject propellants is broken down into three major phases: reject propellant size reduction phase, pentane extraction phase, and separation and purification phase.

The process by phases includes a size reduction phase which comprise:

1. providing reject propellant containing n-hexylcarborane to be extracted;
2. slicing the reject propellant under a flood of water into small pieces (e.g., ⅛ inch thick) to form a water and propellant slurry;
3. collecting water and propellant slurry in a vat provided with a removable cover and containing a removable screen bucket by allowing the sliced propellant and water to collect in the screen bucket;

4. allowing the water to drain from the propellant in the screen bucket and then pumping the water to waste; and, 5. securing the vat cover in place and sealing the vat.

Another phase of the process includes an extraction phase which comprises:

1. venting the vat to a still condenser to prevent loss of pentane solvent during pentane solvent filling; and, 2. filling vat with pentane solvent, agitating to form a slurry mixture, and allowing the reject propellant to soak for a predetermined time up to about 27 hours to extract the n-hexylcarborane from the propellant.

The last phase of the process includes a separator and purification phase which comprises:

1. opening the vat and raising the screen bucket containing the extracted propellant above the vat to allow the n-hexylcarborane/pentane to drain into the vat;

2. transferring the extracted reject propellant into a disposable container;

3. pumping the n-hexylcarborane/pentane solution from the vat through a filter to remove any small suspended particles of propellant and other solids such as ammonium perchlorate;

4. admitting the n-hexylcarborane/pentane solution from the filter to a partially filled water wash tank at the bottom through a dip tube;

5. allowing the n-hexylcarborane/pentane solution to diffuse up through the water in the water wash tank to remove ammonium perchlorate and other water soluble materials and to permit separation of the n-hexylcarborane/pentane solution into a layer on top of the water layer;

6. siphoning the n-hexylcarborane/pentane solution from the water layer and discharging the water to waste disposal;

7. passing the n-hexylcarborane/pentane solution that is siphoned from the water layer through a filter dryer to remove any possible solid material and to dry the solution prior to admitting to the still;

8. admitting the n-hexylcarborane/pentane to a still and concentrating the n-hexylcarborane by flash distilling about 80% of the pentane from the n-hexylcarborane/pentane solution;

9. condensing the pentane and returning the pentane to the pentane storage; and, 10. transferring the 80/20 n-hexylcarborane/pentane solution to an n-hexylcarborane production facility for purification by distilling from an n-hexylcarborane purification still.

Figure 1:
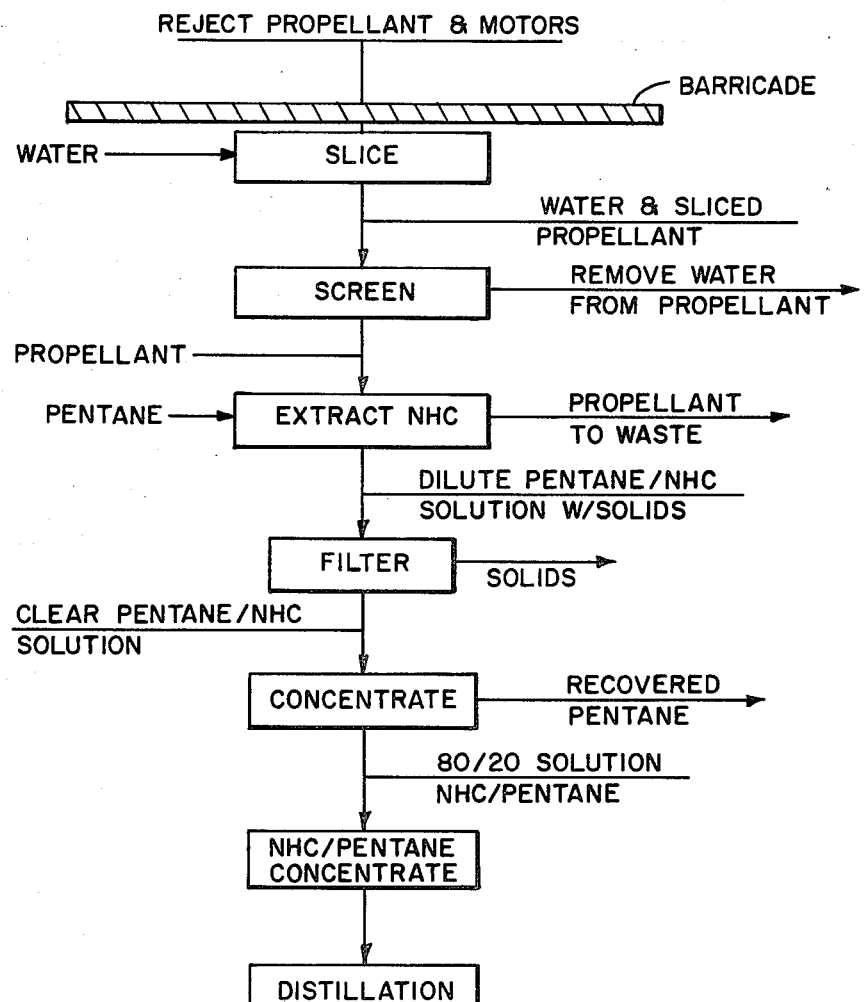
FIG. 1 of the drawing is a flow chart which depicts the steps relating to the process for the recovery of n-hexylcarborane (NHC) from propellant.
Figure 2:
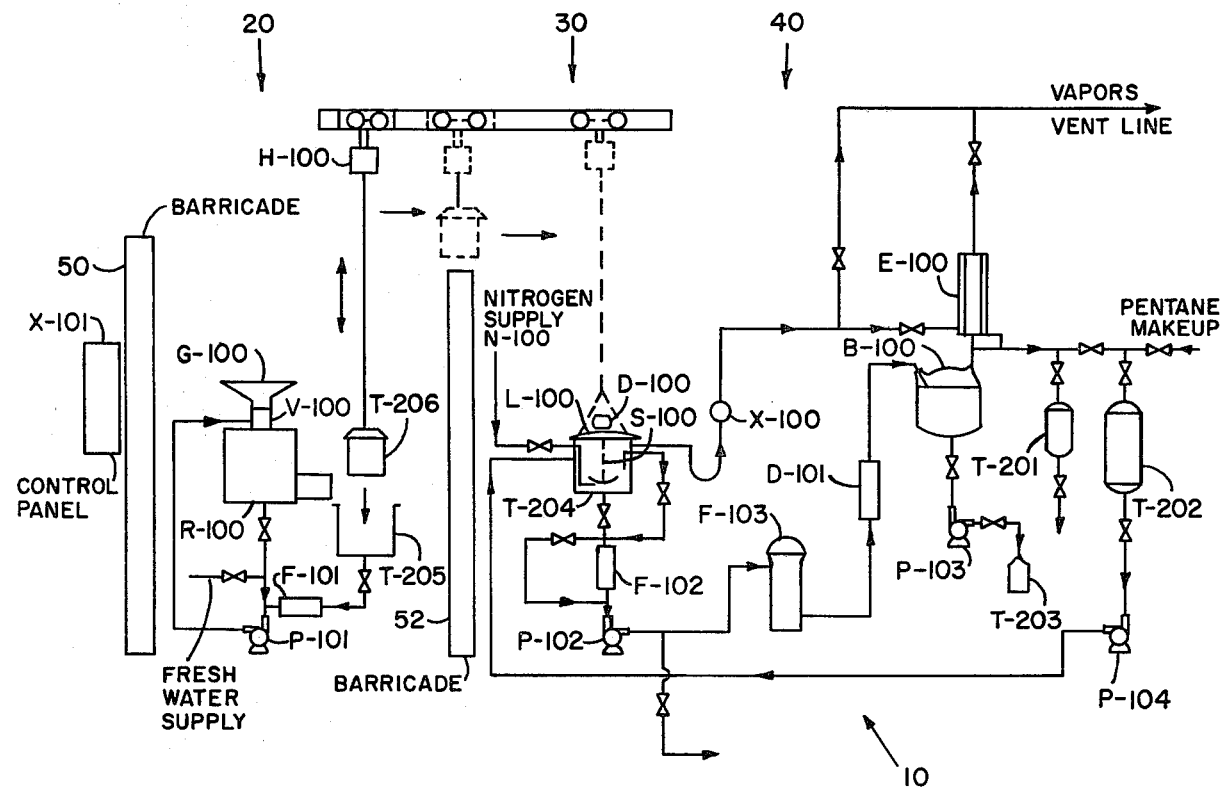
FIG. 2 of the drawing is a flow diagram of a preferred n-hexylcarborane (NHC) recovery process which depicts the equipment associated with the process steps.

In further reference to the drawing, FIG. 2 depicts the flow diagram of n-hexylcarborane recovery process (10) from reject propellant. A preferred design of equipment employed in the reject propellant size reduction phase is shown as 20. A preferred design of equipment employed in the pentane extraction phase is shown as 30. A preferred design of equipment employed in the separation and purification phase is shown as 40.

The description of the procedure employed in the NHC recovery process is further described hereinbelow (under Procedure I, Steps 1-25) wherein reference to the equipment function is made in conjunction with its identity as depicted in FIG. 2.

Procedure I: Recovery of NHC from cured waste propellant:

1. The pentane/NHC solution is pumped by the pentane/NHC solution pump (P102) from the NHC extraction tank (T204) to the pentane recovery still (B100) by way of the pentane/NHC pump filter (F102) NHC/pentane solution filter (F103) and NHC/pentane dryer (D101).

2. When the pentane/NHC solution transfer is completed, the NHC extraction tank (T204) is vented to the waste vent line, and a nitrogen purge line to the NHC extraction tank (T204) is opened to flush all the pentane vapors from the NHC extraction tank.

3. The recovery of the pentane is started by raising the temperature of the pentane recovery still (B100) with hot water. Chilled water will be applied to the pentane condenser (E100) with vent valve to vent line opened.

4. The pentane is collected in the pentane receiver and storage tank (T202).

5. The filter cartridges are removed from the pentane/NHC filter (F103) and the pentane/NHC pump filter and the filters are replaced with new filters. The used filters will be combined with waste propellant for disposal.

6. When the pentane vapors in the NHC extraction tank (T204) has been removed by the nitrogen flushing process, the NHC exterior cover (L100) is removed and raised from the tank by the hoist (H100).

7. The hoist (H100) is brought into place and the propellant screen basket (T206) containing the extracted waste propellants is raised from the NHC extraction tank, and the waste propellant removed from the basket, packaged and prepared for disposal.

8. The waste propellant is removed from the work area.

9. The scrap, waste propellant to be extracted will be collected, inspected and weighed.

10. The propellant shall be cut in several 10 pound batches using the propellant Cutter (R100).

11. Water is circulated through the hopper (G100) and the propellant cutter (R100), and the cut propellant tank (T205) by starting water circulating pump (P101).

12. The propellant screen basket (T206) is placed in position in the cut propellant tank (T205).

13. A charge of propellant (10 pounds) is placed in the propellant hopper (G100).

14. The operator leaves the area and remotely actuates the propellant transfer valve (V100), dropping the propellant into the propellant cutting chamber.

15. The cutter driver motor or actuator is started remotely, and the batch of propellant is cut.

16. Operation 15 is repeated until the total batch of waste scrap propellant has been cut.

17. When the cutting operation is completed, the water circulating pump (P101) is stopped and the propellant screen basket (T206) is raised by hoist from the cut propellant tank (T205) and allowed to drain.

18. When most all of the water has drained from the propellant in the propellant screened basket (T206), the basket is then moved to, and lowered into the NHC extraction tank (T204).

19. The NHC extraction tank cover (L100) is then brought into place over the NHC extraction tank (T204) and sealed on the tank.

20. The NHC extraction tank (T204) is then charged with the necessary amount of pentane, pumped by the pentane pump (P104) from the pentane receiver and storage tank (T202).

21. The waste scrap propellant is then allowed to soak and extract overnight.

22. When the major portion of the pentane has been removed from the pentane/NHC solution in the pentane recovery still (B100) as indicated by pot temperature increase and reflux decreases, the still will be shut down.

23. The NHC in the pentane recovery still (B100) is pumped by way of the NHC pump (P103) to the NHC receiver tank (T203). The NHC is then packaged for shipment to the NHC production facility for purification.

24. If the NHC is to be purified on site, the NHC will be pumped from the pentane recovery still (B100) to an NHC purification still.

25. The propellant cutter (R100) will be cleaned, inspected, and prepared for cutting operations next day.

Although emphasis has been placed on cured, scrap, water propellant, uncured propellant can be extracted equally well. The desirability of also recovering NHC from uncured waste propellants is quite clear since a valuable product can be recovered with fewer steps than the process of recovery from cured reject propellant. For example, cutting is not necessary for the uncured rejected propellant and therefore, this material should be extracted separately in the NHC extraction vat. The uncured propellant is added to the NHC extraction tank and the stirrer shaft attached so that the uncured propellant can be stirred in the pentane solvent. After a short period of stirring, the stirrer is stopped and the propellant allowed to settle to the bottom of the extraction tank. The pentane/NHC solution is siphoned from the propellant in the tank and pumped through the filter and dumped into the pentane recovery tank. When the pentane/NHC solution has been removed from the tank, water is added to the extraction tank, and the stirrer is started to dissolve the solid oxidizer. The water/polymer/Al solution/slurry is then pumped to the waste disposal area for burning.

Under Procedure II: Recovery of NHC from uncured waste propellant, a description is given of the process by step 1–11 wherein reference is made to the equipment function in conjunction with identity as depicted in FIG. 2. The size reduction phase 20 is not required for the recovery of NHC from uncured propellant.

Procedure II:

Recovery of NHC from uncured waste propellant.

1. With the NHC extraction tank cover (L100) removed from the NHC extraction tank (T204) along with the propellant screened basket (T206), the waste, uncured propellant is poured into the NHC extraction tank (T204).

2. The stirrer shaft (S100) is fastened in place in the stirrer motor drive (D100) mounted on the lid of the NHC propellant extraction tank (T204). (Use teflon stirrer).

3. The NHC extraction tank cover (L100) is then lowered in place and the cover fastened in place.

4. Pentane is pumped from the pentane receiver and storage tank (T202) into the NHC extraction tank (T204).

5. The stirrer motor (D100) is started and run approximately 15 to 20 minutes to slurry the propellant in the pentane.

6. The stirrer motor is stopped and the solid propellant phase allowed to separate from the pentane. The propellant will settle to the bottom of the NHC extraction tank.

7. When separation is complete, the NHC extraction tank is then pressurized with $N_2$ forcing the pentane NHC solution from the NHC extraction tank (T204) into the pentane/NHC pump (P102) for transfer through the pentane/NHC filter (F102) and dryer (D101) into the pentane recovery still (R100).

8. The pentane is recovered from the pentane NHC solution as has been described.

9. When the pentane/NHC solution has been transferred from the NHC extraction tank (T204) water is added to the tank and the stirrer motor shaft (S101) started.

10. Water will dissolve the solid oxidizer in the propellant and this slurry containing aluminum powder along with polymeric materials is pumped from the NHC extraction tank to waste storage for final waste disposal.

11. The NHC extraction tank cover (L100) is removed from the NHC extraction tank (T204), the tank cleaned and prepared for the next extraction operation.

Table I below lists the solvent pentane, size of propellant cure condition, agitation, if any, % NHC recovered, and extraction time for NHC recovery from propellant. The size reduction to about ⅛ inch thick slivers with an extraction time of about 27 hours yielded a 100% NHC recovery. A shorter extraction time for uncured propellant is required for 100% NHC recovery.

TABLE I

NHC RECOVERY FROM PROPELLANT

| | SAMPLE | | | | |
|---|---|---|---|---|---|
| | 1 | 2 | 3 | 4 | 5 |
| SOLVENT | PENTANE | PENTANE | PENTANE AND WATER | PENTANE | PENTANE |
| DIMENSION | BLOCKS | STICKS | SLIVERS | LIQUID | LIQUID |
| | 1" × 1¼" × 2⅜" | ¼" × 5/16" × 1¾" | ⅛" × ⅛" × ⅛" | | |
| CURE | CURED | CURED | CURED | UNCURED | UNCURED |
| AGITATION | NONE | NONE | NONE | ONLY AT BEGINNING OF EXPERIMENT | NONE |
| NHC RECOVERED % | 88 | 100 | 100 | 100 | 100 |
| TIME HOURS | 72 | 27 | 27 | 24 | 72 |

*PROPELLANT EXTRACTED OVER NIGHT. NO ANALYSES WERE RUN BETWEEN THE BEGINNING OF THE EXTRACTION AND 24 HOURS.

For safety purposes concrete barricades 50 and 52 are employed as shown in FIG. 2 of the drawing so that operations of the process can be controlled remotely from control panel X-101, as also shown in FIG. 2.

Other identities and functional elements shown in FIG. 2 include a nitrogen supply N-100 for purging system. A propellant transfer valve V-100 is provided to remotely control the propellant as required for the slicer or cutter operation. An agitator vapor trap X-100 is depicted between extraction tank T-204 and the pentane condenser E-100. A waste pentane tank T-201 is provided which is also provided with a valve to permit draining for disposal or other purposes. The process system is provided with a pentane makeup supply and a fresh water supply as illustrated in FIG. 2.

Table II provides a listing of major equipment which is identified by item number as shown by drawing, FIG. 2. The size and material of construction along with a description thereof is provided for the equipment suggested for a 2550 pounds/year recovery of NHC.

TABLE II

MAJOR EQUIPMENT LIST

| ITEM | DESCRIPTION | SIZE AND MATERIALS OF CONSTRUCTION |
|---|---|---|
| R-100 | Propellant cutter | Fabricated - chamber 8.5 in. diameter, 12 in. long. Piston - screw driver - electric motor explosion proof material of construction. Teflon and stainless steel. |
| T-205 | Cut propellant tank | Stainless steel - 80 gallon working capacity with rim inside to support propellant screen basket. Bottom sump drain connection |
| T-204 | NHC extraction tanks | 100 gallon. 75 gallon working capacity. |
| T-201 | Waste pentane tank | 20 gallon capacity. Carbon steel. |
| T-202 | Pentane receiver and storage tank. | 200 gallon capacity. Carbon steel |
| T-203 | NHC receiver | 50 gallon capacity. Stainless steel. |
| T-206 | Propellant screen basket | Stainless steel - 8 cu. ft. Approximately 60 gallons. |
| P-101 | Water circulating pump | 5 gallon/minute. Paired for safety. |
| P-102 | Pentane/NHC solution pump | 5 gallon/minute |
| P-103 | NHC pump | 5 gallon/minute |
| P-104 | Pentane pump | 5 gallon/minute |
| F-101 | Water pump filter | 2 cu. ft. Paired. 5 gallon/minute flow. Replaceable cartridge. |
| F-102 | Pentane/NHC pump filter | 1 cu. ft. Paired. 5 gallon/minute flow. |
| F-103 | Pentane/NHC solution filter | 2 cu. ft. 5 gallon/minute flow. Replaceable cartridge. |
| D-101 | NHC/Pentane solution dryer | 1 cu. ft. 5 gallon/minute. Replaceable cartridge. |
| B-100 | Pentane recover still | 100 gallon capacity. Jacketed. |
| E-100 | Pentane condenser | Chilled water. |
| G-100 | Scrap propellant hopper | 2 cu. ft. |
| H-100 | Hoist | 2000 pounds |
| D-100 | Stirrer motor | ½ HP |
| N-100 | Nitrogen supply | Liquid $N_2$ Storage or high pressure cylinder bank. |
| V-100 | Propellant transfer valve | |
| X-100 | Agitator vapor trap | |
| X-101 | Motor/instrument control panel | Fabricated. |
| T-207 | Organic waste holding tank | 250 gallon capacity |
| T-208 | Aqueous waste tank | 500 gallon capacity |

Table III below lists the physical and chemical properties of n-hexylcarborane. These properties are based on high purity NHC. These properties provide guidelines for the conditions required for recovery and the equipment design.

TABLE III

PHYSICAL AND CHEMICAL PROPERTIES OF N—HEXYLCARBORANE

| | |
|---|---|
| Molecular Weight (Grams/mole) | 222.48 |
| Molecular Formula | $C_8H_{24}B_{10}$ |
| Melting Point °C. | −6 |
| Boiling Point °C. at 0.1 torr | 120 |
| Density (Grams/cc) 20° C. | 0.981 |
| Color | Pale yellow |
| $H_f$Cal at 25° C. Kcal/mole | −91 |
| Pounds/gallon | 7.66 |
| Refractive Index $n_D^{20}$ | 1.5219 |

Table IV below lists the physical and chemical properties of chemicals involved in the process of this invention.

TABLE IV

PHYSICAL AND CHEMICAL PROPERTIES OF PROPELLANT AND CHEMICALS INVOLVED

| Ingre- | Density | | MP | | BP | |
| dient | g/cc | lb/cu in | °F. | °C. | °F. | °C. |
|---|---|---|---|---|---|---|
| Propellant | 1.720 | 0.0620 | — | — | — | — |
| Pentane | 0.630 | 0.0227 | −200 | −129.7 | 97. | 36.3 |
| NHC | 0.980 | 0.354 | +21.2 | −6° | 248. | 120° at 1/mm Hg |

The cost effectiveness of the process of this invention is readily recognized after reviewing the NHC recovery cost as depicted hereinbelow in Table V. The present production cost is several times the cost for recovery which includes additional purification cost for NHC; therefore, based on a recovery of about 2550 pounds per year, an NHC recovery facility could be amortized in a few years. With a greater amount of propellant to process, the amortization time would be proportionately less.

TABLE V

NHC RECOVERY COST

| | | Cost/Year |
|---|---|---|
| CHEMICALS | | |
| Solvents - Pentane | 2500 pounds/year | $2,500 |
| Other | | 500 |

TABLE V-continued
NHC RECOVERY COST

| | Cost/Year |
|---|---|
| OPERATING LABOR TOTAL | $3,000 |
| Operators 2 manyears 4160 hours $7.00/hour | 29,120 |
| Supporting labor - maintenance, safety supervision, analytical, etc. 100% direct labor | 29,120 |
| TOTAL | $58,240 |
| Overhead 150% direct | 87,360 |
| Maintenance Materials and Supplies 15% direct labor | 8,735 |
| Utilities | 6,300 |
| Packaging and shipping | 5,000 |
| TOTAL DIRECT COST | $168,635 |
| 2550 pounds/year NHC (Direct recovery cost) = | 66.13/lb |
| G & A 25% | 16.53 |
| SUBTOTAL | 82.66 |
| Fee 10% | 8.25 |
| TOTAL recovery cost/lb | $90.91 |
| Recovery cost per lb based on recovery of 2550 pounds/year of crude NHC. Purification cost must be added. | $90.91 |

So that recovered NHC as compared to commercial, high purity NHC is evaluated in propellant compositions, propellant compositions employing reference NHC and commercial, high purity NHC were made for evaluations. Table VI, Example 1 below, shows data which ascertains that recovered NHC can be employed in propellant with equal reliability to achieving the propellant properties required.

TABLE VI
COMPARISON OF RECOVERED NHC IN PROPELLANT COMPOSITIONS WITH REFERENCE NHC
EXAMPLE NO 1

| | REFERENCE NHC LOT 110977 | RECOVERED NHC LOT 70677 |
|---|---|---|
| COMPOSITION | | |
| NHC purity | 99.6 | 99.5 |
| PROPELLANT PROPERTIES | | |
| End of Mix Viscosity Kpoise at 120° F. | 1.0 | 1.2 |
| Pot Life Viscosity Kpoise 2 hours at 120° F. | 1.1 | 1.3 |
| Burning rate in/sec 2000 psi | 6.14 | 6.17 |
| Pressure Exponent | .60 | .60 |
| Sensitivity | | |
| Friction-angle 75° 8 ft/sec 600 psi no fires at lbF/in$^2$ | 5.7 × 10$^{-4}$ | 5.7 × 10$^{-4}$ |
| Impact | | |
| No fires inches | 12.57 | 11.33 |
| 50% fire level inches 2 kgwt | | .66 |
| DTA 10° C./min Heating Rate | | |
| Endotherm °C. | 243 | 242 |
| Exotherm °C. | 322 | 307 |
| Mechanical Properties +77° F. | | |
| Stress psi | 358 | 368 |
| Strain % | 22 | 23 |
| Modulus psi | 2255 | 2247 |
| −40° F. | | |
| Stress psi | 987 | 881 |
| Strain % | 21 | 23 |
| Modulus psi | 7600 | 6332 |

Table VII, Example 2 below, sets forth a typical propellant formulation to further evaluate the results obtained when recovered NHC is employed as compared to production NHC when it is employed. The propellant properties data show that recovered carborane is equal to the production carborane in propellant performance.

TABLE VII
COMPARISON OF RECOVERED NHC WITH PRODUCTION NHC
EXAMPLE No 2

| INGREDIENTS | LOT # | MIX 104-403* WT % | MIX 104-404** WT % |
|---|---|---|---|
| HTPB | 3921 | 7.66 | 7.66 |
| BA114 | 20175 | .30 | .30 |
| TMP | 1975-31 | .06 | .06 |
| NHC | PL8246 | 6.00 | — |
| NHC | 31 | — | 6.00 |
| AL | 5214 | 15.00 | 15.00 |
| UFAP | VMA-151 | 47.50 | 47.50 |
| AP | LAWT | 22.50 | 22.50 |
| TPB | 61976 | .03 | .03 |
| IPDI | 4440 | .98 | .98 |
| EOM Viscosity 120° F. | | 1.8 | 1.8 |
| Viscosity after 2 hrs pot life 145° F. | | 2.5 | 2.3 |
| Burn Rates 2000 psi in/sec | | 6.58 | 6.57 |
| Physical Properties +77° F. | | | |
| Stress psi | | 344.6 | 331.7 |
| Strain % | | .212 | .222 |
| Modulus psi | | 2221 | 2088 |
| −40° F. | | | |
| Stress psi | | 975. | 953.2 |
| Strain % | | .217 | .202 |
| Modulus psi | | 6954 | 6857 |

*MIX 104-403 represents recovered NHC
**MIX 104-404 represents production NHC
HTPB Hydroxy-terminated polybutadiene
BA114 Bonding Agent, formulated of equimolar quantities of 12-hydroxystearic acid and tris[1-(2 methyl)-aziridinyl]phosphine oxide.
TMP Trimethylol propane
NHC n-Hexycarborane
AL Aluminum
UFAP Ultrafine ammonium perchlorate
TPB Triphenyl bismethine
IPDI Isophorone diisocyanate, (crosslinking agent, curative)

Based on the NHC recovery data, and the results of the extraction of a significant quantity of propellant, it appears that amounts from about 85% to 100% of the NHC can be recovered from cured and uncured reject propellant and that the quality of the recovered NHC is equal to that of the NHC production lots.

Figure 3:
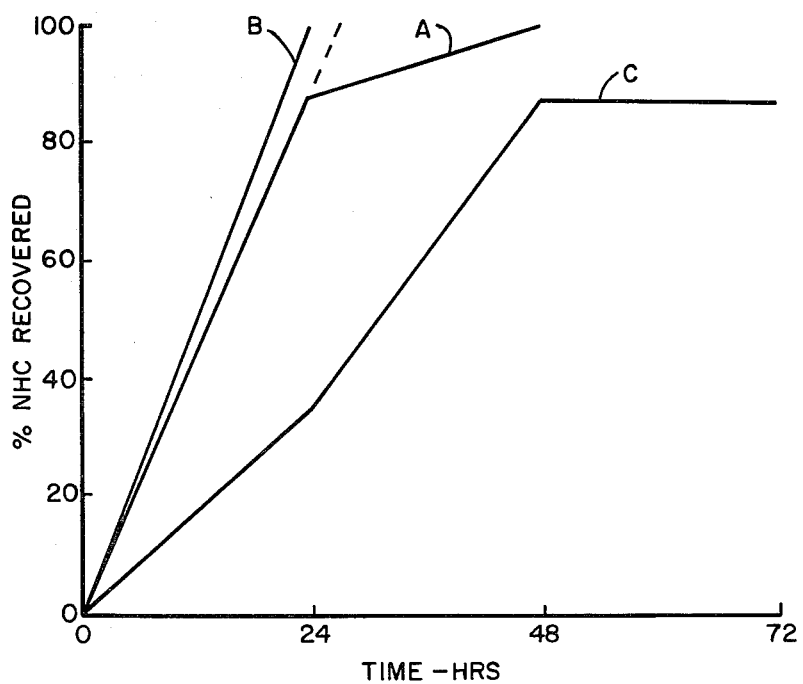
FIG. 3 of the drawing is a curve based on the time of extraction plotted against % NHC recovered for various size reductions of scrap propellants, cured and uncured.

In further reference to FIG. 3 of the drawing, curve A depicts a size reduction of reject cured propellant to about $\frac{1}{8}''\times\frac{1}{8}''\times\frac{1}{4}''$, an extraction time of about 24 to about 48 hours, and a % NHC recovery approaching about 100%. Up to about 85% of the NHC is recovered after an extraction period of about 24 hours. About 100% is recovered after total soaking time of about 27 hours for the preferred size of about $\frac{1}{8}$ inch thickness (see Example 3, Table I).

Curve B of FIG. 3 depicts the NHC recovery from uncured propellant of about $\frac{1}{4}''\times 5/16''\times 1\frac{3}{4}''$ which indicates that about 100% of the NHC is recovered by an extraction time of about 24 hours.

Curve C of FIG. 3 depicts the NHC recovery from cured propellant of about $1''\times 1\frac{1}{4}''\times 2\frac{1}{2}''$ which indicates that a longer extraction time of up to about 48 hours is required for larger sized propellant pieces for an NHC recovery of about 88%.

The majority of the pentane is recovered for reuse from the filtered pentane/NHC extract solution by flash distillation. The flash distillation serves to concentrate the NHC. The purification phase of NHC requires vacuum distillation which removes additional pentane. The vacuum distillation provides for a lower pot temperature which is an advantage for the safety aspects of the purification phase.

Although the major fraction of the extract is NHC, some of the low molecular weight polymeric binder and other minor ingredients may be extracted with the NHC and will be left as pot bottoms when the NHC is distilled. The NHC will distill at 120° C. at 0.1 mm Hg pressure with a pot temperature in the order of 165° C.

The safety aspects of the distillation as the pot bottoms concentration increases were evaluated by running impact and friction tests on the pot bottoms. In addition DTA tests were run in order to determine if exothermic reactions would take place and at what temperature they would occur. This data is summarized in Table VIII below and compared with the sensitivity characteristics of neat NHC. The results show that the data is in agreement between safety aspects of neat NHC and pot bottoms after the distillation of recovered NHC.

Gas chromatographic analysis of recovered NHC compared with reference lot showed an assay of 99.6 for reference and compared with 99.5 for the recovered. Thus there is no reason to believe that NHC extracted from the propellant would not be as good as that from production. Any materials extracted with the NHC from the propellant and remained in the recovered NHC as impurities would be materials that were part of the propellant and should be compatible with the propellant formulation on reuse of the recovered NHC.

TABLE VIII

SAFETY EVALUTION OF POT BOTTOMS AFTER THE DISTILLATION OF RECOVERED NHC

|  | POT BOTTOMS | NEAT NHC |
|---|---|---|
| Friction sensitivity 15.6 × 10$^{-4}$ at 2000 psi (16f/in$^2$ × 10$^{-4}$) (Maximum capacity of the apparatus) | Negative 100% | Negative 100% |
| Impact Sensitivity 49.9 with 2Kg wt. (Maximum height of apparatus) | Negative 100% | Negative 100% |
| DTA 10° C./min heating rate Endotherm °C. | None Slow rise beginning at 202° C. | None Slow rise beginning at 240° C. |

I claim:

1. A process for the recovery of n-hexylcarborane from reject propellant comprising:

(i) providing a quantity of reject propellant containing n-hexylcarborane to be recovered;

(ii) adding said reject propellant to an extraction vat provided with a removable propellant screen bucket, a removable cover for said extraction vat, agitator means for mixing said reject propellant with an extraction solvent, a means for filling and draining said extraction solvent, a means for venting said extraction vat, and a means for purging said extraction vat with an inert gas, said means for venting being in fluid communication with a condenser for said extraction solvent;

(iii) securing said removable cover and opening said venting means to said condenser means to prevent loss of said extraction solvent during the filling of said extraction vat with said extraction solvent;

(iv) filling said extraction vat with an extraction solvent selected from pentane and hexane, said extraction solvent being in excess of said quantity of reject propellant provided;

(v) agitating said reject propellant and said extraction solvent to form a slurry mixture of said reject propellant and said extraction solvent;

(vi) allowing said reject propellant to soak for a predetermined time period of up to about 27 hours to extract said n-hexylcarborane from said reject propellant;

(vii) opening said vat and raising said screen bucket containing said extracted reject propellant above said vat to allow said n-hexylcarborane/extraction solvent solution to drain into said vat;

(viii) transferring said extracted reject propellant to disposal;

(ix) pumping said n-hexylcarborane/extraction solvent solution from said extraction vat through a filter to remove any small suspended particles of propellant and other solids;

(x) admitting said n-hexylcarborane/extraction solvent solution from filter to a partially water filled wash tank, said n-hexylcarborane/extraction solvent solution admitted at the bottom of said tank through a dip tube;

(xi) allowing said n-hexylcarborane/extraction solvent solution to diffuse up through the water in said wash tank to remove ammonium perchlorate and other water soluble materials and to permit separation of said n-hexylcarborane/extraction solvent solution into a layer on top of the water layer;

(xii) siphoning said n-hexylcarborane/extraction solvent solution from the water layer and discharging the water to waste disposal;

(xiii) passing said n-hexylcarborane/extraction solvent solution that is siphoned from the water layer through a filter dryer to remove any possible solid material and to dry the solution prior to transferring to a still;

(xiv) transferring said n-hexylcarborane/extraction solvent solution to a still and concentrating the n-hexylcarborane by flash distilling about 80% of the extraction solvent from said n-hexylcarborane/extraction solvent solution;

(xv) condensing the extraction solvent and then returning said extraction solvent to an extraction solvent storage for reuse; and, (xvi) transferring the 80/20 n-hexylcarborane/extraction solvent solution to an n-hexylcarborane production facility for purification by distilling from an n-hexylcarborane purification still.

2. The process of claim 1 wherein said reject propellant is a cured solid propellant that is subjected to a size reduction phase prior to said adding to said extraction vat, said size reduction phase comprising:

(i) slicing said reject propellant under a flood of water into small pieces of about ⅛ inch maximum thickness to form a water and propellant slurry;

(ii) collecting said water and propellant slurry in a vat provided with a removable cover and containing a removable screen bucket by allowing the sliced propellant and water to collect in the screen bucket;

(iii) allowing the water to drain from said water and propellant slurry in said screen bucket and then pumping the water to waste; and, (iv) recovering said small pieces of reject propellant from which n-hexylcarborane is to be extracted.

3. The process of claim 2 wherein said extraction solvent selected is pentane.

4. The process of claim 1 wherein said reject propellant is uncured and wherein said extraction solvent is pentane.

* * * * *